United States Patent [19]

McDonald

[11] 4,253,457
[45] Mar. 3, 1981

[54] UROLOGICAL ENDOSCOPIC IRRIGATION SYSTEM

[76] Inventor: Harold P. McDonald, 3544 Paces Ferry Rd., NW., Atlanta, Ga. 30327

[21] Appl. No.: 63,652

[22] Filed: Aug. 3, 1979

[51] Int. Cl.³ .............................................. A61M 7/00
[52] U.S. Cl. ..................................... 128/227; 137/403
[58] Field of Search .................. 128/227, 229, 214 R, 128/230; 137/403

[56] References Cited

U.S. PATENT DOCUMENTS 3,578,774   5/1971   McDonald, Jr. ..................... 128/227

Primary Examiner—John D. Yasko

Attorney, Agent, or Firm—Allison C. Collard; Thomas M. Galgano

[57] ABSTRACT

A urological endoscopic irrigation system which consists of a reverse osmosis unit adapted for connection to an available hospital supply to produce at its output an available supply of nonpyrogenic water. The water is fed through a dionization chamber and final sterile filter into a reservoir bag which is supported on a weight switch so that the bag will be filled with a predetermined amount of filtered and nonpyrogenic fluid for use by a cystoscope. A reservoir and pump may be provided in the output line of the reverse osmosis unit to provide additional fluid capacity for the cystoscope.

7 Claims, 2 Drawing Figures

UROLOGICAL ENDOSCOPIC IRRIGATION SYSTEM

This invention relates to an improved urological irrigation apparatus for use during endoscopy of the bladder and urethra or for postoperative therapy of the patient.

More specifically, this invention relates to a urological irrigation apparatus which is capable of utilizing conventional tap water as an irrigant, and after passing the water through suitable filtration devices, providing it in measured amounts to the patient during endoscopy or postoperative therapy.

Conventional devices which provide irrigation fluid for urological endoscopy are presently considered inefficient. In one type of system, Valentine flasks which are bulky, fragile and awkward, are sterilized and filled with a steril fluid for connection to the patient. The top of the Valentine flask generally remains open as the fluid is dispensed to the patient so that organisms from the environment can contamminate the fluid. Moreover, when the Valentine flasks have to be refilled, additional sterilized irrigation fluid has to be added from heavy, bulky bottles which have to be lifted above head height in order for their contents to empty into the flasks.

In another conventional system which attempts to overcome the above-described disadvantages, commercially prepared solutions are provided in large disposable containers which have to be stored under controlled conditions. These containers occupy valuable hospital space before they are utilized. Many conventional devices combine some of the features of both of the above-described apparatus, and have been found to be complex and excessively expensive for occasional hospital use.

In another conventional device described in the applicant's prior U.S. Pat. No. 3,578,774, an irrigation apparatus is provided which is capable of holding a supply of nonpyrogenic hospital distilled water in controlled amounts. The distilled water is pumped through a tube into a reservoir bag at an elevated height. A membrane filter is connected to the input of the bag to filter out bacteria from the distilled water and the bag is supported from a weight sensitive switch which is responsive to the weight of the bag and its contents. At the bottom of the bag is connected an endoscopy tube which is used for treatment of the patient so that as the fluid leaves the reservoir bag, the weight sensitive switch will automatically operate the pump to refill the bag with distilled water from the reservoir so as to maintain a constant supply of irrigation fluid for the patient.

This patented system however requires an available supply of nonpyrogenic distilled water to fill the reservoir and further requires daily maintenance and cleaning of the reservoir tank and the apparatus.

Accordingly, the present invention overcomes many of the disadvantages of the above-described conventional devices by providing a self-contained apparatus which requires little or no maintenance and provides an immediate and continuous supply of endoscopic irrigation fluid without requiring a set up of external apparatus. In the invention, a reverse osmosis fluid supply is connected to the available water supply or tap water so as to provide a filtered nonpyrogenic supply of water for use by the patient. The reverse osmosis filter has a primary filtration element which receives a continuous flow of water so that the filter is self-cleaning and the contaminents will pass through the filter into the discharge pipe. The filter may include a pump which is responsive to a weight sensitive switch that supports a reservoir bag so that a constant supply of water can be maintained in the bag by the pump operating on the filter. In another embodiment of the invention, a dionization chamber can be connected to the input of the reservoir bag to remove pyrogens and ions to improve the purity of water entering the reservoir. Moreover, a final sterile filter such as a Millipore sterilizing filter can be included after the ionization chamber to provide a final filtration of the water entering the reservoir bag. In still a further embodiment, a separate reservoir can be connected between the reverse osmosis unit and the dionization chamber so as to store a supply of nonpyrogenic water before it is pumped into the reservoir bag. The pump at the reservoir or the pump at the osmosis unit or both can be connected to the weight sensitive switch which supports the bag to maintain a constant water level in the bag.

The reservoir bag is never completely filled in order to provide an air space near its top. Therefore, air bubbles which become entrapped in the filtered and sterilized water will have an opportunity to collect near the top of the bag, and the endoscopic irrigation fluid which is drawn from the bottom of the bag will be free of entrapped air.

It is therefore an object according to the present invention to provide an improved endoscopic irrigation apparatus which permits the use of an available supply of conventional water for use in postoperative therapy or endoscopy.

It is another object according to the present invention to provide a simplified endoscopic irrigation apparatus which is easy to manufacture, and reliable in operation.

Other objects and features of the present invention will become apparent from the following detailed description considered in connection with the accompanying drawing which discloses the embodiments of the present invention. It is to be understood, however, that the drawing is designed for the purpose of illustration only and not as a definition of the limits of the invention.

In the drawing wherein similar reference characters denote similar elements throughout the two views.

Figure 1:
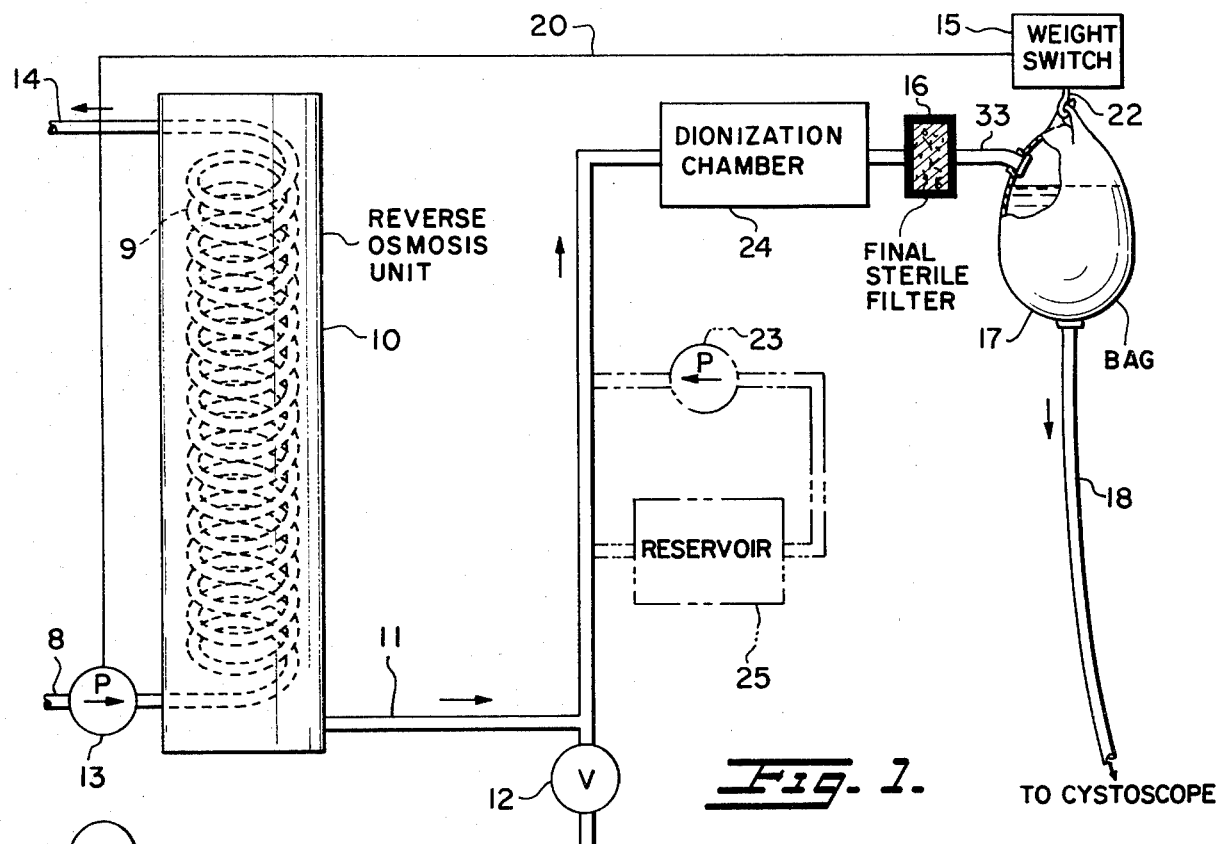
FIG. 1 is a perspective view of one embodiment of the invention.

Referring to FIG. 1 there is shown a reverse osmosis unit 10 connected to an input water line 8 and including a pump 13 for controlling the flow of tap water into the primary coil of the unit. The unit may include a coil 9 as shown disposed within its jacket or a straight pipe, having an output or return pipe 14 mounted at its opposite end. With tap water being used, pipe 14 would allow the water to drain into a waste pipe. Generally, the reverse osmosis unit would include a restriction or venturi at its effluent outlet in order to increase the static pressure within coil 9 of the unit. The coil is preferably constructed of a porous metallurgical material which is corrosion resistant and permits only fluid particles on the order of tenths of a micron to pass into the secondary portion of the filter to be collected by collection tube 11 mounted near the bottom of the unit. A valve 12 may be used to tap into pipe 11 to sample or drain the fluid contants at the output of reverse osmosis unit 10. The output of pipe 11 is preferably connected to a dionization chamber 24 which may or may not be used in the system. If the chamber is used, it will remove some pyrogens and ions, and provides an improved purity of the water. The chamber is approximately 1 inch to 1½ inches in length and about 1 inch in diameter.

The output of dionization chamber 24 is coupled to the input of a final sterile filter 16 which is preferably a filter having a porosity of 0.3 microns or less and of a membrane type to insure final sterility. The final filter and dionization chamber (if used) are disposable and discarded after each used or after several uses. The output 33 of filter 16 is connected near the top of a reservoir bag 17 which collects the filtered water. Bag 17 is preferably supported on a hook 22 which is connected to a weight switch 15. Switch 15 is normally closed, and becomes open when a predetermined weight is placed on hook 22. The weight switch can be set to permit approximately 2500 cubic centimeters of fluid to fill reservoir bag 17 before becoming open circuited. At the bottom of bag 17 is connected an endoscopy tube 18 which is then connected to a cystoscope for postoperative therapy.

Weight switch 15 can have its electrical input connected to a standard 110 volts AC line (not shown) so that its output line 20 can be connected to pump 13 which controls the fluid through the primary coil of reverse osmosis unit 10. As the fluid is removed from bag 17 through tube 18, weight switch 15 will apply power to pump 13 until a sufficient amount of nonpyrogenic water refills bag 17. The bag is designed to be disposable so that it can be discarded after one or several uses.

In an additional embodiment of FIG. 1, a reservoir 25 may be added to pipe line 11 to store the output of reverse osmosis unit 10 so that the stored output can be added to line 11 by means of a pump 23 as required. In this embodiment, pump 23 would be electrically connected to line 20 of weight switch 15.

Figure 2:
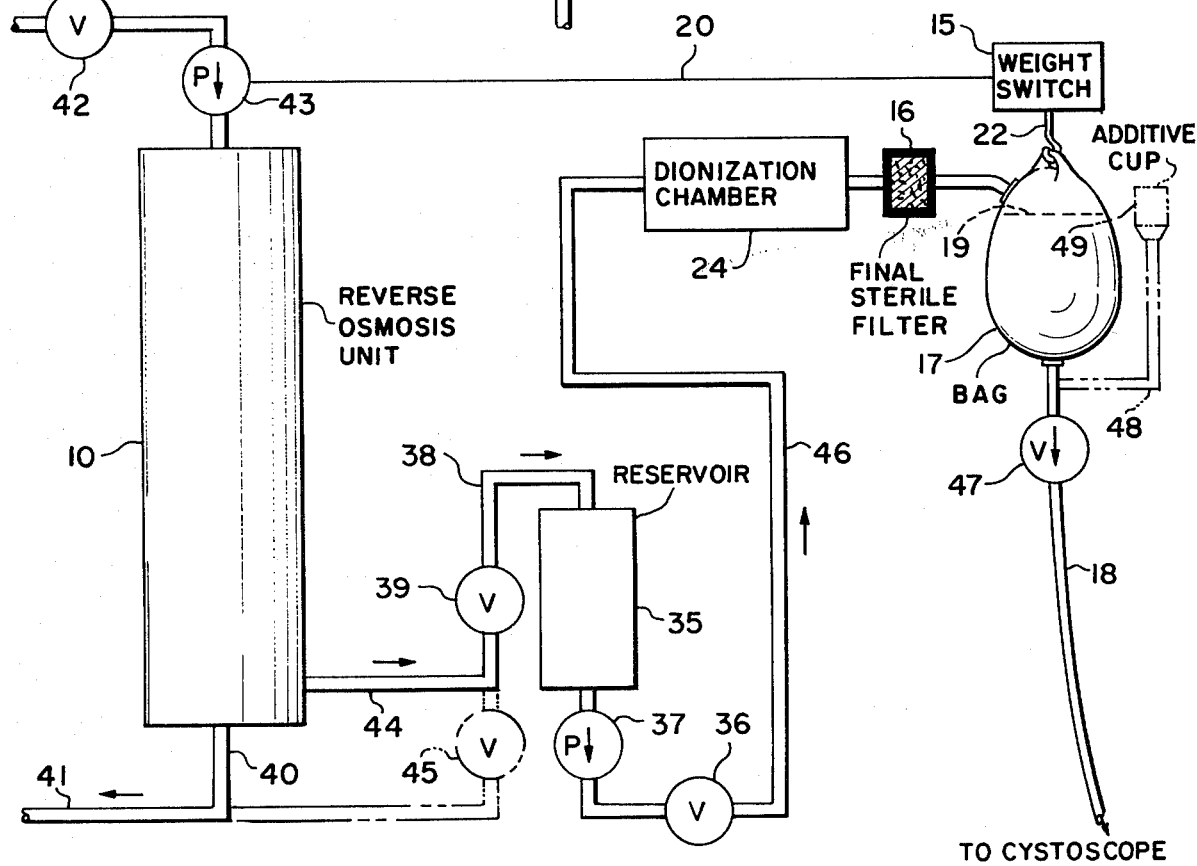
FIG. 2 is a perspective view showing another embodiment of the invention.

FIG. 2 shows another embodiment of the invention wherein the inlet main stream or influent enters valve 42 and is pumped by means of pump 43 through reverse osmosis unit 10 before exiting from effluent pipe 40 into outlet line 41. The secondary outlet 44 of unit 10 is fed into open valve 39 which is connected by means of pipe 38 to the input of reservoir 35. At the output of reservoir 35 is a pump 37 to pump the nonpyrogenic water supply from the reservoir, through open valve 36, into the dionization chamber. The dionization chamber 24, final filter 16 and bag 17 operate in a manner similar to that described with respect to FIG. 1. However, at the output of bag 17 is connected a one-way valve 47 before connection to endoscopy tube 18. In addition, an additive cup 49 can be connected through line 48 to the output of bag 17 so that additional fluids such as glycerine, sorbitol or mannitol may be added. It should also be noted that the additive cup 49 could be incorporated into the system prior to the final sterile filter. In addition, instead of being a cup, it may be designed as a pump assembly so as to positively inject the additives into the system.

Bag 17 operates weight switch 15 similar to that of FIG. 1 so that pump 43 will operate to keep a level of fluid maintained in bag 17. Weight switch 15 can also be connected to pump 37 in order to move sterile water from reservoir 35 into the bag.

The apparatus of FIGS. 1 and 2 particularly the reverse osmosis unit, dionization chamber and final filter can be maintained in a wall cabinet together with their associated valves and pumps so that no separate apparatus has to be set up for each use. The reservoir bag together with its associated weight switch can be easily coupled adjacent to the patient on a stand and connected back to the cabinet or wall unit located adjacent to the patient's bed.

The use of disposable components such as the dionization chamber, final filter and reservoir bag simplify the maintenance of this system of the present invention.

It should also be pointed out that it is possible to sterilize the entire system by heat or chemical sterilization such as Formalin solution.

While only a few embodiments of the present invention have been shown and described, it will be obvious that many changes and modifications may be made thereunto without departing from the spirit and scope of the invention.

What is claimed is:

1. An irrigation apparatus for dispensing fluid comprising:
    a reverse osmosis unit for connection to a conventional water supply for producing a substantially pyrogen-free fluid;
    final filter means coupled to the output of the reverse osmosis unit for filtering the fluid supply collected by the osmosis unit;
    reservoir container means coupled to the output of said filter means for holding a measured quantity of the fluid; and
    weight sensitive switch means supporting said reservoir container means whereby actuation of said switch means transfers quantities of fluid from said reverse osmosis unit to said reservoir container means 2. The irrigation apparatus as recited in claim 1 wherein said filter means comprises a dionization chamber connected to the output of said reverse osmosis unit and a sterilizing Millipore filter.

3. The irrigation apparatus as recited in claim 1 additionally comprising a reservoir connected to the output of said first osmosis unit for storing a quantity of nonpyrogenic fluid.

4. The irrigation apparatus as recited in claim 1 additionally comprising an additive cup coupled to the output of said reservoir container means to permit the addition of chemicals to the endoscopic fluid.

5. The irrigation apparatus as recited in claim 4 additionally comprising a one-way valve coupled to the output of said reservoir container means.

6. The irrigation apparatus as recited in claim 3 wherein said reverse osmosis unit additionally comprises a drain valve coupled to its output for draining the nonpyrogenic fluid.

7. The irrigation apparatus as recited in claim 1 additionally comprising pump means connected to a source of power with said switch means interposed between said pump and said source of power whereby actuation of said switch means transfers quantities of fluid from said reverse osmosis unit to said reservoir container means.

* * * * *